United States Patent
Dubé

(10) Patent No.: US 8,850,742 B2
(45) Date of Patent: Oct. 7, 2014

(54) SYSTEM FOR MODULATING PLANT GROWTH OR ATTRIBUTES

(75) Inventor: Sylvain Dubé, Borås (SE)

(73) Assignee: Heliospectra AB, Gothenburg (SE)

( * ) Notice: Subject to any disclaimer, the term of this patent is extended or adjusted under 35 U.S.C. 154(b) by 1048 days.

(21) Appl. No.: 12/529,350

(22) PCT Filed: Mar. 20, 2008

(86) PCT No.: PCT/SE2008/050316
§ 371 (c)(1),
(2), (4) Date: Sep. 3, 2009

(87) PCT Pub. No.: WO2008/118080
PCT Pub. Date: Oct. 2, 2008

(65) Prior Publication Data
US 2010/0115830 A1    May 13, 2010

(30) Foreign Application Priority Data
Mar. 23, 2007  (SE) ...................... 0700721

(51) Int. Cl.
*A01G 9/00* (2006.01)
*A01G 31/00* (2006.01)
*G01N 21/64* (2006.01)
*A01G 7/04* (2006.01)
*G01N 21/63* (2006.01)

(52) U.S. Cl.
CPC ............ *G01N 21/6486* (2013.01); *A01G 7/045* (2013.01); *G01N 2021/635* (2013.01)
USPC ................................ 47/17; 47/60

(58) Field of Classification Search
USPC ............................................ 47/60, 61, 69, 17
See application file for complete search history.

(56) References Cited

U.S. PATENT DOCUMENTS

| 4,051,626 A | * | 10/1977 | Trumley et al. ................... 47/17 |
| 4,701,415 A | * | 10/1987 | Dutton et al. .............. 435/286.6 |
| 4,768,390 A | | 9/1988 | Baker |

(Continued)

FOREIGN PATENT DOCUMENTS

| DE | 10137360 A1 | 2/2003 |
| JP | 5-153871 | 6/1993 |
| JP | 2001-28947 | 2/2001 |

OTHER PUBLICATIONS

Written Opinion and International Search Report issued in parent PCT application.

*Primary Examiner* — Monica Williams
(74) *Attorney, Agent, or Firm* — Harness, Dickey & Pierce

(57) ABSTRACT

A system (1) for modulating growth or attributes of at least one part (2) of one or more plants comprising chlorophyll is disclosed. The system (1) comprises at least one light emitting device (3), such as a light emitting diode (LED), for irradiating the at least one part (2), at least one light sensor (4) for picking up light from the at least one part (2), communication capabilities (5) for facilitating communication between the at least one light sensor (4), the at least one light emitting device, and a processor (6). The processor (6) reads data from the at least one light sensor (4) via the communication capabilities (5), generates a control signal based on the data and a reference, and then controls, based on the control signal, the at least one light emitting device (3) via the communication capabilities in order to modulate plant growth or plant attributes.

21 Claims, 1 Drawing Sheet

(56) References Cited

U.S. PATENT DOCUMENTS

| | | |
|---|---|---|
| 5,253,302 A | 10/1993 | Massen |
| 5,299,383 A * | 4/1994 | Takakura et al. .......... 47/58.1 R |
| 5,946,852 A * | 9/1999 | Oram et al. ................ 47/58.1 R |
| 6,880,291 B2 * | 4/2005 | Raun et al. ............... 47/58.1 SC |
| 2003/0005626 A1 | 1/2003 | Yoneda |
| 2003/0146394 A1 * | 8/2003 | Prange et al. .............. 250/458.1 |

* cited by examiner

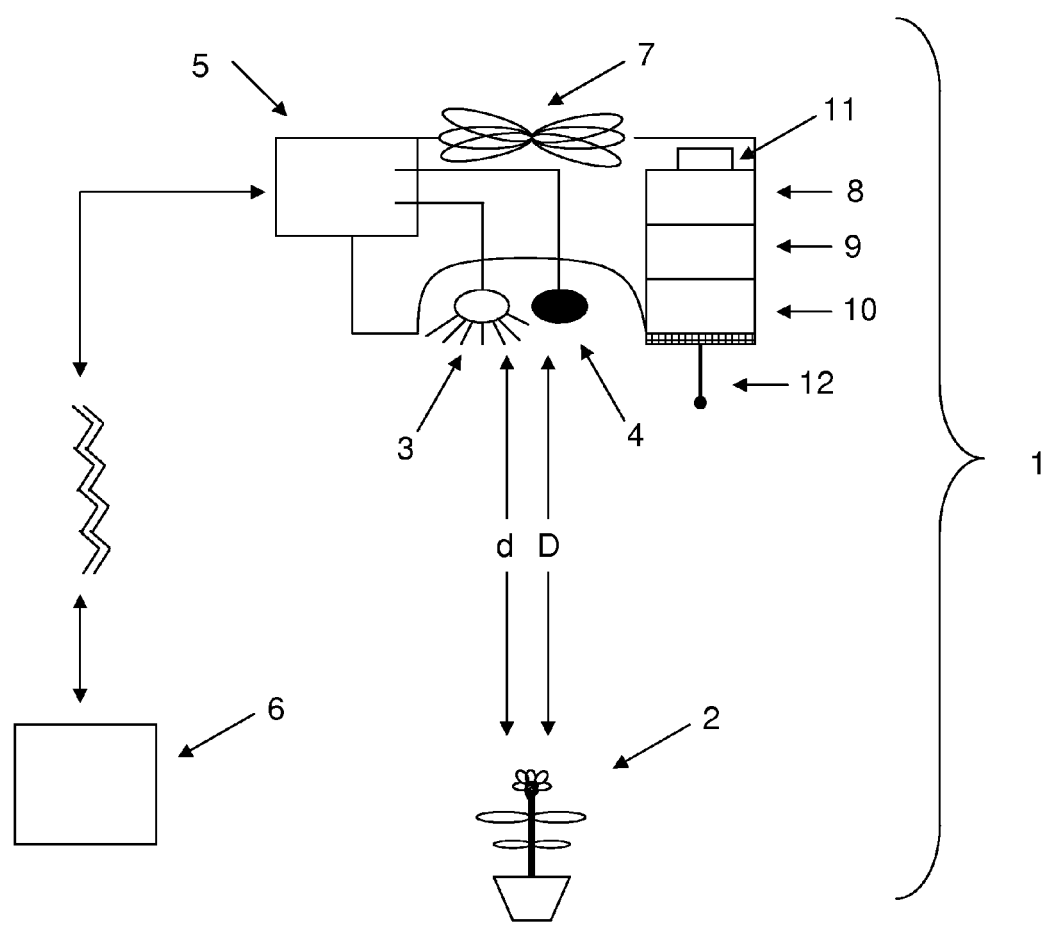

SYSTEM FOR MODULATING PLANT GROWTH OR ATTRIBUTES

TECHNICAL FIELD

The present invention relates to a system for modulating growth or attributes of at least one part of one or more plants comprising chlorophyll.

SUMMARY OF INVENTION

Growing plants under controlled conditions such as in greenhouses, growth cabinets or warehouses, generally consists of monitoring the plant environment and controlling parameters such as light, water vapor pressure, temperature, $CO_2$ partial pressure, and air movement, in order to adjust the microclimate of the environment for optimizing growth and photosynthesis in an empirical manner. Plant attributes may also be modulated and these may include quantitative morphological, physiological and biochemical characteristics of at least a plant part.

It is important in many areas of plant husbandry to have the ability to determine the physiological condition of a plant or group of plants in order to implement photosynthetic responses into climate control algorithms or models. Optimization of photosynthesis of crops or plant material can be achieved through careful and planned manipulations of growth conditions based on in situ monitoring of relevant photosynthetic processes. Relevant and short term plant responses are involved in the definition of growth requirements not only through climate control but also the production processes, fertilizers, light quality and intensity, crop quality. All these responses will ultimately affect economic returns. For example, the forestry industry replants millions of seedlings every year. These seedlings are initially grown in a controlled environment and are transplanted into the field during very specific and critical periods during seedling development. However, in the case of evergreen conifers it is difficult to determine by physical appearance alone when seedlings have reached the physiological state when they can be successfully transplanted outside. In addition, it can be difficult to determine from external plant appearances whether or not the light quality and intensity in a controlled environment is optimal for plant health and economic returns. Similarly, early determination of plant stress, effects of fertilizer and water regimes, grazing and effects of physical damage on the plant's vigor is difficult if not impossible to determine based on the external appearance of the plant. By the time the stress is physically apparent the crop can be beyond a critical point of recovery.

To effectively control the climate, irrigation, nutrition and light regime of greenhouse crops in order to beneficially modulate and control growth and attributes of crops one needs to incorporate "plant sensors" as well as models into the feed-forward/feedback component of the system. Feed-forward controllers such as lamp light output provide necessary input for plant growth and have the capacity to anticipate the effects of disturbances on the greenhouse climate and in the light environment and take action within precisely set limits. Specific crop models, developed for individual crop species, should be based on data from plant stress sensors and growth monitoring sensors (crop sensors) and should be able to estimate the benefits of changing growth regimes (eg spectral quality of the light source) to influence or modulate the outcome (eg flowering time). The data obtained by the crop sensors is combined with model based algorithms (soft sensors) and this in turn directs the specific changes in light intensity and/or quality which will beneficially influence the plant's growth processes or attributes.

This invention relates generally to a system for modulating plant growth or their attributes by 1) measuring plant environment parameters such as temperature, barometric pressure, relative humidity, $CO_2$, light, and plant biochemical attributes, 2) communicating the results of analysis, and 3) controlling the system using a feed-forward/feed-back loop. This invention modulates plant growth and/or attributes of at least one part of at least one plant containing chlorophyll in a self-sustaining manner. It achieves this by altering morphological and/or biochemical characteristics, e.g. photosynthesis, hormone regulation, secondary metabolites and properties of at least one part of at least one plant comprising chlorophyll, for managing crops in terms of plant growth or their attributes in terms of economic returns.

According to the present invention a system for modulating growth or attributes of at least one part of one or more plants comprising chlorophyll is disclosed. The system comprises:
  at least one light emitting device, such as a light emitting diode (LED), for irradiating the at least one plant part,
  at least one light sensor for picking up light surrounding the at least one part,
  communication capabilities for facilitating communication between the at least one light sensor, the at least one light emitting device, and
  a processor.

The term picking up light includes picking up irradiance, reflected light, and re-emitted light from the at least one plant part. In an embodiment, the at least one light emitting device is situated at a minimum distance "d" from the light emitting device. In embodiments, 'd' is one of 20, 30, 40, 50, 60, 70, 80, 90, 100, 110, 120, 130, 140, 150 cm. In an embodiment, the at least one light sensor is situated at a distance "D" from the light sensor (4). In embodiments, 'D' is one of 20, 30, 40, 50, 60, 70, 80, 90, 100, 110, 120, 130, 140, 150 cm.

The processor reads data from the at least one light sensor via the communication capabilities. The processor generates a control signal based on the data and a reference, and that signal controls, based on the control signal, the at least one light emitting device, such as a light emitting diode (LED), for irradiating the at least one plant part via the communication capabilities in order to modulate or improve growth and/or attributes.

In an embodiment, the control signal offers an opportunity to become a part of climate control of greenhouses, e.g. an opportunity of altering the $CO_2$ partial pressure, in the case where the system comprises a $CO_2$ partial pressure control device. The control signal controls the climate such that the growth of a plant and its attributes are modified. Non limiting objects of the invention include improving the quality of plant, growth and growth rate.

In an embodiment, the system further comprises an external light sensor for picking up neighboring light.

In an embodiment, the reference is a 'should reference' which may be static. A 'should reference' comprises a light frequency setting describing what frequency/frequencies at what time(s). The data may be seen as an input to potentially change the light outputted by the at least one light emitting device. In case of several light emitting devices emitting light with different frequency characteristics, the control signal comprises control in terms of which light emitting device, which light intensity and the duration and also what frequency the light emitting device should emit.

In an embodiment, the reference may be dynamic in the sense that the reference may change during the course of plant growth and development. The object of the reference is to operate as a controlling means leading to improved growth and alteration of attributes by adjusting the control signal. In an embodiment, the reference is based on algorithms which are based on combined experimental and theoretical data.

In an embodiment, the reference is based on at least one of chlorophyll fluorescence and/or leaf light reflectance. Thus chlorophyll fluorescence and/or leaf light reflectance are parameters that may be used as inputs to the reference. This will lead to that the control signal will be affected by at least one of the chlorophyll fluorescence and/or leaf light reflectance parameters. This leads to modulation of growth and modulation of plant attributes.

According to the present invention, only a part of a plant, or the canopy, or a whole plant, or several plants may be monitored by and subjected to the system. The control generated by the processor may be used to control other plants or parts thereof.

Advantages of the present invention include the following:

- It takes into consideration the higher efficiency of electrical energy conversion into light energy with the desired light spectral characteristics.
- It contributes to the decrease in $CO_2$ gas emissions by the greenhouse industry because it uses light more effectively for growing crops.
- It contributes to a decrease in atmospheric light pollution from the greenhouse industry by only using light spectral characteristics that are mostly absorbed and used by plants.
- It provides a means for checking or evaluating a plants ability to respond to growing conditions or to changes thereof (eg. more or less light or even varying light spectral quality).
- It allows continuous remote monitoring by means of monitoring photophysical, photochemical and photosynthetic parameters since it circumvents the problems of altering the local environmental conditions with probes delimiting a restricted leaf sampling area.
- It allows "learning" with the plants own requirements for achieving the plants best performance in aimed growing conditions with the use of an artificial neural network system.
- It may be used to determine the precise location, based on the location of sensors, of stress induced by water deficiency, nutrient deficiency or excess, virus, fungi or bacteria, insects and arachnids.
- Levels of water stress may be indicated.
- Effects of toxic compounds and herbicides may be indicated.
- Screening of photosynthetic mutants amongst a population of plants of unknown makeup may be done.
- Using the present invention leads to improved taste and flavor attributes of greenhouse (or indoor) grown crops.
- Also, using the present invention leads to saving electrical energy input by optimizing/minimizing crop light reflectance. This is achieved by measuring with a light sensor while maintaining photochemistry between optimal and maximal photosynthetic capacity. Optimal capacity is being defined as a situation where photosynthesis and growth are at optimum while maximal capacity is any situation where energy is also used in the generation of aromatic and protective compounds.

In an embodiment, the system further comprises a plurality of light emitting devices. This offers the advantage of being able to have a more complex reference. In an embodiment, the plurality of the light emitting device emits light with different frequency characteristics. In an embodiment, the emitted and/or reflected light is related to at least one characteristic parameter of the photosynthetic process.

In an embodiment, the light sensor measures at least one light intensity corresponding to a wavelength of at least one of R (Red, 630 to 700 nm), FR (Far Red, 700 to 740 nm), NIR (Near Infrared, 750 to 850 nm), IR (Infra-Red, 850 to 1400 nm), or PAR (photosynthetically active radiation) (400 to 700 nm). In these ranges the light may deal with fluorescence emission from a part of a plant comprising chlorophyll.

In an embodiment, the light sensor measures at least one light intensity corresponding to a wavelength of BG (Blue Green, 400 to 630 nm). In these ranges the light may deal with fluorescence emission from a part of a plant comprising UV-shielding compounds and/or NADPH production or content.

In an embodiment, the light sensor measures at least one light intensity corresponding to a wavelength of NIR (Near Infrared, 750 to 850 nm). In these ranges the light may deal with light reflectance from a part of a plant comprising light not absorbed by the chlorophylls.

In and embodiment, the light sensor measures at least on light intensity corresponding to a wavelength of IR (850 to 1400 nm). In these ranges the light may deal with light reflectance representing cellular and structural arrangement of plant leaves, and moisture content.

In an embodiment, the light sensor measures at least one light intensity corresponding to a range of wavelength between 400 and 700 nm. In this range the light may deal with light corresponding to the definition of PAR or Photosynthetically Active Radiation.

In an embodiment, the monitored light is related to measuring at least one biochemical process from at least one biochemical substance.

In an embodiment, the system further comprises at least one fan for accomplishing airflow in relation to the at least one plant part and the control signal further comprising a fan signal control. The intention is to introduce air movement to induce thigmomorphology and for disturbing the leaf boundary layer (for mixing the gas composition around the leaves to increase transpiration, water, $CO_2$ uptake and favor photosynthesis).

In an embodiment, the at least one fan is located near the at least one light emitting device for accomplishing a cooling of the at least one light emitting device.

In an embodiment, the at least one light sensor may measure either fluorescence, incident, or reflected light of the same wavelength interval.

In an embodiment, the system may further comprise one or more gas meters for measuring gas levels (eg $CO_2$ and Relative Humidity) in the air surrounding the at least one plant part. The meter(s) is located within a measuring distance in relation to the at least one plant and is connected to the processor.

In an embodiment, the system further comprises an air flow meter for measuring the air speed in close proximity of the at least one plant part, the air flow meter being electrically connected to the processor, and a temperature sensor for measuring temperature of the air surrounding the at least one plant part. The temperature sensor is electrically connected to the processor.

BRIEF DESCRIPTION OF DRAWINGS

In FIG. 1, a schematic illustration of the system is shown.

EMBODIMENTS

In FIG. 1, a schematic illustration of the system 1 is shown. The system 1 measures and/or modulates plant growth and attributes of at least one plant part 2 of one or more plants comprising chlorophyll. In an embodiment, the system 1 measures biochemical and photochemical properties. The system 1 comprises at least one light emitting device 3, in an embodiment a diode (LED), for irradiating the at least one part 2 and at least one light sensor 4 for picking up light from the at least one part 2. Also, the system 1 comprises communication capabilities 5 for facilitating communication between the at least one light sensor 4, the at least one light emitting device 3 for irradiating the at least one part 2, and a processor 6. The processor 6, comprises a control unit that reads data from the at least one light sensor 4 via the communication capabilities 5, generates a control signal based on the data and a reference, and controls, based on the control signal, the at least one light emitting device 3 via the communication capabilities 5 in order to improve plant growth and attributes.

In an embodiment, the system 1 comprises a plurality of light emitting devices 3 and they emit light with different frequency characteristics. The plurality of light emitting devices 3 may be located either separately or located together on a common supporting structure.

In an embodiment, the light is related to at least one characteristic parameter of the photosynthetic process or at least one biochemical substance.

In embodiment, the light sensor measures at least one light intensity corresponding to a wavelength of at least one of:
BG (Blue Green, 400 to 630 nm)
R (Red, 630 to 700 nm),
FR (Far Red, 700 to 740 nm),
NIR (Near Infrared, 750 to 850),
IR (Infra-red, 850 to 1400 nm), and
PAR (Photosynthetically Active Radiation, 400 to 700 nm).

In an embodiment, the system 1 further comprises at least one fan 7 for accomplishing an airflow in relation to the at least one plant part and the control signal further comprising a fan control signal. In order to receive the fan control signal, the at least one fan is connected to the communication capabilities 5, which may be LAN, WLAN, or a communication cable in line with the inventiveness of the skilled person. In an embodiment, the fan is located in the lamp housing and may be activated by a dedicated fan control 11.

In an embodiment, the at least one fan is located near the at least one light emitting device for accomplishing active or forced air cooling of the at least one light emitting device.

In an embodiment, the at least one fan is located distantly to the at least one light emitting device for accomplishing a cooling of the at least one light emitting device.

In an embodiment, the system comprises arrays of high power, high efficient LEDs having 9 ranges (or subsets or clusters) of wavelengths from UV-B to IR. Also, there are 9 independent drivers for energizing and controlling each range of LEDs independently. Each array comprises a microprocessor to control the LEDs in a DC or pulse amplitude modulated (PAM) current controlled circuit. For each range the driver can be user programmable to change the frequency and the duty cycle of the modulation.

In an embodiment, temperature sensors are placed at relevant positions to monitor temperature at near junction of the LED chips (Tj). In an embodiment, each range of LEDs is placed on the circuit/substrate board in such a way as to distribute the heat load. The microprocessor (s) can be programmed to switch off the driver (s) if the estimated junction temperature is above a maximum operating temperature. In an embodiment, there is an environmental monitoring system connected to the present system. The environmental monitoring system has ambient air thermometer, ambient light sensors, gas sensors ($CO_2$, Relative Humidity, others). For example, as shown in FIG. 1, one or more gas meters for measuring $CO_2$ 8 and relative humidity (9) levels in the air surrounding the at least one slant part can be located within a measuring distance in relation to the at least one plant part and being connected to the processor (6). FIG. 1 also illustrates an air flow meter (10) for measuring the air flow in close proximity of the at least one plant part and a temperature sensor (12) for measuring temperature of the air surrounding the at least one plant part. The air flow meter and temperature sensor are connected to the processor (6).

In an embodiment, photodiodes mounted with specific color filters are included in the system.

In an embodiment, CCD camera (charged coupled device camera) or other imaging device is mounted with a step motor controlled filter wheel.

In an embodiment, the at least one light emitting device may be provided with a housing that has reflectors to illuminate a predefined pattern of light and light area. Also, it has baffles on the housing in order to support the creating of air turbulence around the leaves. In an embodiment, one or more of the fans may be used to create an air flow cooling the lamp. The housing also leads to that light emitting device effectively transmits heat. In an embodiment the housing presents an opening at an end of the housing opposite to the direction of the light emitted from the lamp(s). The opening allows air to flow therethrough leading to a cooling effect within the light emitting device.

In an embodiment, sensors are located in the housing or near a light emitting device.

The processor controlling the lamp(s) is designed to provide the following embodiments.

The LEDs may pulse at maximum current to obtain maximum light for a time interval. Non limiting examples of time intervals include, 1-3 seconds, and 0.5 to 5 seconds.

The LEDs are able to be driven in modulated mode, so called "pulse-width modulated power waveform". The duty cycle being the variable, is capable of varying the output power of the LEDs with sharp rise and fall times while the current is maintained constant. The on-time should be ranging from 20 µs to 2.5 ms. In an embodiment, the off-time does not exceed 500 µs.

The LEDs are able to be driven at their typical electrical characteristics on a continuous mode (DC).

The LEDs are able to be driven in a pulse mode with 4-5 times their nominal typical current value, while providing effective cooling.

In an embodiment, the system further comprises at least one means of communicating output from measured sensors and communicating control signals to the at least one LED connected to the communication capabilities, which may be LAN, WLAN, or a communication cable in line with the inventiveness of the skilled person.

In an embodiment the plant physiology and morphology is altered to favor height, branching, specific leaf area, phenology and plant biomass.

In an embodiment, the plant biochemical attributes are modulated to alter the content of aromatic substances of aromatic crops.

In an embodiment, crop yield is monitored and communicated instantaneously on a continuous basis.

In an embodiment, crop yield (growth) is managed according to the knowledge and management of the electrical power input of the system.

In an embodiment, any alteration will be specific to the individual needs to the grower and based on the specific crop requirements.

In an embodiment, the synthesis of chlorophyll and/or accessory pigments is up- or down-regulated in order to modify the biochemical attributes resulting in a change in leaf coloration of the crop.

In an embodiment, the initial fluorescence parameter, Fo, is determined by a light sensor. This achieved by controlling a light emitting device in the absence of (other) ambient light. While, in the presence of ambient light Fo is estimated from the chlorophyll index measured as the logarithm of $R_{800}/R_{550}$, where R is reflectance and 800 and 550 are wavelengths in nm. Light reflectance R is being measured by light sensor 4.

In an embodiment the system use machine vision and multispectral reflectance image processing to determine: Top Projected Canopy Area of several plants (TPCA) and Top Projected Leaf Area of one plant (TPLA).

In an embodiment the system may be used to provide the means of identifying photosynthetic mutants by analysing their sensitivity to photoinhibition by measuring $\Phi_{PSII}$ before and after an irradiation stress generated by extended exposure to intense light. Also, it provides means for enabling the development of mutants requiring conditional environmental treatments (elevated PAR, low PAR, blue light, red light, UV light, elevated $CO_2$).

In an embodiment the system may be used to provide the means for increasing leaf thickness, developing epicuticular wax and stomatal regulation.

In an embodiment there will exist a number of algorithms.

A first embodiment of a control algorithm is based on chlorophyll fluorescence which allows a non intrusive, non-destructive and repetitive assessment of in vivo photosynthesis evaluation, providing data on the overall photosynthetic quantum yield capacity through the quantification of Fv/Fm, photosystem II photochemical efficiency $\Phi_{PSII}$ and the fluorescence quenching coefficients. The use of variable fluorescence for determining the extent of physiological stress of growing plants is a sensitive, reliable, universal tool, to characterize the plants ability to use delivered photons.

Inputs to the control algorithm include parameters such as Fo, Fm, Fp, Ft (Fs), F'm and F'o of plants to provide values for the calculation of index values such as Fv/Fm, Fv/Fo, $\Phi_{PSII}$, Fs/Fo, F'v/F'm and quenching coefficients such as NPQ, $q_N$ and $q_L$. The system provides means of inducing and measuring variable chlorophyll fluorescence of plants situated under the lamp (which may be a delimited area) at wavelengths such as 440, 690 and/or 735 nm chlorophyll fluorescence. The system continuously optimizes growing conditions in order to obtain rapid growth rates and a high acclimatization index through the proper and continuous balance between non-photochemical quenching NPQ, $q_N$ and photochemical quenching $q_L$ of chlorophyll fluorescence.

Inputs to the control algorithm include parameters such as changes in stomatal conductance. A correlation exists between Fs and stomatal conductance. With this correlation the proper monitoring of Fs would be a useful tool for deciding when irrigation must be applied to maintain the plant at a limit between water stress and excess water consumption. Also, it provides means for evaluating stomatal closure capacity by monitoring transpiration in darkness and/or through the response in changes in transpiration rates upon application of specific light treatments of delimited spectral quality. Also, the system can provide signals to increase $CO_2$ partial pressure in the growing environment provides means for decreasing $g_s$ (stomatal conductance) to improve water status for facilitating upcoming transplantation. The variables used to evaluate stomatal conductance are:

1. $F_o$ (initial or fast Chlorophyll fluorescence measured in the dark adapted state),
2. $F_t$ and/or $F_s$ (slow or steady state variable Chll fluorescence (seconds to hours).

In an embodiment a control algorithm is based on a neural network (NN), implemented within the system. The models obtained by the NN provide identification and control systems specific to the plant species, stage of growth, capacity for growth under specifically programmed growing conditions. The models obtained by the NN will be used to predict short-term and long-term responses and performance of various plants. Such an algorithm provides means for achieving plants best performance within a determined period of time. It also provides means for rapidly detecting and identifying plants that are not achieving the predicted (expected) best performance. Also, it provides means for predicting growth and "time to reach harvest time" or time and cost to obtain "minimal quality criteria" from the parameters obtained from trained NN data. It is to be trained from experimental crop data and by monitoring:

1. Leaf temperature
2. Quantum yield of $CO_2$ assimilation
3. Irradiance
4. Variable fluorescence
5. The plants stage of growth
6. Plants changes in growth rates
7. Estimates of chlorophyll content
8. Estimates of UV-shielding compounds
9. Estimates of LAI (Leaf Area Index)
10. TPCA (Top Projected Leaf Canopy Area)
11. PRI (Photochemical Reflectance Index PRI=(R531−R570)/(R531+R570)
12. Chlorophyll Index as the log of R800/R550
13. "Green" NDVI (Normalized Difference Vegetation Index)=(nir−g)/(nir+g) where "nir" is light reflectance at 800 nm and "g" is light reflectance at 550 nm.
14. Plant species and/or cultivar.

In an embodiment of the system the control algorithm is based on treatments for inducing stomatal opening. The system provides means for inducing stomatal aperture control by applying light radiation of wavelength in the UV A or blue region (peak at 450 nm) without the need for inducing photosynthesis with broadband (polychromatic) light which would otherwise decrease water use efficiency in incompetent leaves. Blue light alone or in combination with red light stimulates stomatal opening in several plants and green light reverses the process and closes the stomata. The inputs in this embodiment are the following:

1. Wind speed, or air movement speed, or mass flow of air flowing around the leaves
2. Estimation of leaf Temperature
3. Ambient light irradiance
4. Broadband light radiation INITIAL or TOTAL (from UV to IR) in absence of leaves or in the presence of plants Broadband light REMAINING
5. Irradiance or PAR (Photosynthetically Active Radiation (400-700 nm))
6. Variable chlorophyll fluorescence (3 different time scales)
7. Multi spectral reflectance of the crop/leaves under the lamp
8. Other gases sensor(s) (presence or not and concentration, rate of increase)
9. Temperature of growth area.

In an embodiment of the system the control algorithm is based on treatments for inducing stomatal opening and measuring photosynthesis. The inputs in this embodiment are the following:

1. Wind speed, or air movement speed, or mass flow of air flowing around the leaves
2. Estimation of leaf Temperature
3. Ambient light irradiance
4. Broadband light radiation INITIAL or TOTAL (from UV to IR) in absence of leaves or in the presence of plants Broadband light REMAINING
5. Irradiance or PAR (Photosynthetically Active Radiation (400-700 nm))
6. Variable chlorophyll fluorescence (3 different time scales)
7. Multi spectral reflectance of the crop/leaves under the lamp
8. Other gases sensor(s) (presence or not and concentration, rate of increase)
9. Temperature of growth area.

In an embodiment a control algorithm is based on a procedure for the determination of Acclimatization Index by way of determining photochemical efficiency of Photosystem II fluorescence ($\Phi_{PSII}$) of plants growing under the lamps:

$$\Phi_{PSII}=[F_m-F'_m]/F'_m$$

1. First, the oxidation of the electron transport chain is achieved by exciting the plant exposed to the light source by turning ON for a few seconds with the part of the light source comprising the IR emitting light only.
2. To obtain $F_m$, an intense flash of excitation light is obtained by turning ON with maximal or sufficient power to device controlled DC-4 and with all colour range (CR1 to CR8) set to turn ON for a flash of light of duration from 0.5 to 1.5 sec, (typically <1 sec). This flash of light of known ($I_{TOTAL}$) intensity is used to obtain an induced maximal peak of variable chlorophyll fluorescence ($F_m$) from the plants under the lamp.
3. Growing lights are set to stay ON and plants are allowed to reach steady state photosynthesis and variable fluorescence kinetics to reach $F_s$.
4. Another intense flash of excitation light is obtained by turning ON with maximal or sufficient power to device controlled DC-4 and with all colour range (CR1 to CR8) set to turn ON for a flash of light of duration from 0.5 to 1.5 sec, (typically <1 sec). This flash of light of known intensity is used to obtain an induced maximal peak of variable chlorophyll fluorescence ($F'_m$) from the plants under the lamp.
5. The values of $F_m$ and $F'_m$ are applied to calculate $\Phi_{PSII}$.
6. The procedure from 1 to 7 is repeated several times daily, or at any other desired interval, and every value is tagged with a time reading.
7. The fluorescence Acclimatization Index is obtained by evaluating the evolution of $\Phi_{PSII}$ in the following manner:

$$AI_{PSII}=(\Phi_{PSII\,t2}-\Phi_{PSII\,t1})/(t_2-t_1)$$

8. From the values obtained, a decision is being taken as to continue or alleviate or discontinue the Acclimatization Inducive Stress. The relative speed of change towards a negative value or a negative value may imply a non successful adaptation to a given stress, while a positive value indicates an improvement on the acclimatization scheme procedure.

Any or all of the control algorithms include the input of following variables:

1. $[I_{TOTAL}-I_{REMAINING}]=I_{ABS}$ by the plant material
2. $F_o$ (initial or fast Chlorophyll fluorescence measured in the dark adapted state)
3. $F_{max}$ (variable Chlorophyll fluorescence at maximal peak (0.5-1.5 sec, typically <1 sec) from dark adapted state
4. $F'_o$ (fast Chlorophyll fluorescence measured in the light adapted state)
5. $F'_{max}$ (variable Chlorophyll fluorescence at maximal peak (0.5-1.5 sec, typically <1 sec) from light adapted state
6. $F_t$ and/or $F_s$ (slow or steady state variable Chll fluorescence (seconds to hours).

Parameters calculated routinely or calculated several times per day from the input variables:

1. $F_V/F_M=[F_{max}-F_O]/F_{max}$
2. $\Phi_{PSII}$ (photochemical efficiency)$=[F_{max}-F'_{max}]/F'_{max}$
3. NPQ or $q_N$ non-photochemical quenching of variable Chlorophyll fluorescence
4. $q_L$ or $q_P$ photochemical quenching of variable Chlorophyll fluorescence
5. Fs/Fo
6. $\Sigma I_{TOTAL}$
7. $\Sigma I_{ABS}$
8. TPCA
9. LAI
10. RGR Relative Growth Rate of the crop and/or individual plants Parameters obtained from the input variables followed over time:

1. $I_{ABS}$=measure of biomass and biomass increase
2. inst$\Phi_{CO2}$=Quantum yield of $CO_2$ assimilation=$P_n/I_{ABS}$
3. $R_D$ (Respiration in the dark)=$[CO_2out_D]-[CO_2in_D]$
4. $M\Phi_{CO2}$=Quantum yield of $CO_2$ assimilation=$[P_{n2}-P_{n1}]/[I_{o2}-I_{o1}]$
5. $g_s$ stomatal conductance
6. $F_V/F_M=[F_{max}-F_O]/F_{max}$
7. $\Phi_{PS2}$ (photochemical efficiency)=$[F_{max}-F'_{max}]/F'_{max}=1-[F_s/F'_{max}]$
8. $q_N$ non-photochemical quenching of variable Chlorophyll fluorescence $$q_N=1-F'm-F'o/Fm-Fo$$

9. NPQ Non photochemical quenching of variable Chlorophyll fluorescence $$NPQ=Fm/F'm-1$$

10. $q_L$ coefficient of photochemical fluorescence quenching $$q_L=q_P\times F'o/F'$$

11. WUE Water Use Efficiency
12. RGR Relative growth and growth rates, diurnal variation in leaf growth Devices controlled (DC) by the system:
1. Fan for Cooling
2. Lights on-lights off
3. Spectral regions of light (ON/OFF and variable)
   CR1=UV B
   CR2=UV A
   CR3=Blue
   CR4=Blue Green
   CR5=Green
   CR6=Orange
   CR7=Red
   CR8=Deep-Red
   CR9=Near Infra-Red 4. Flash of intense polychromatic light radiation (frequency and duration)
5. Air movement (fan) for disturbing the leaf boundary layer (of air)
6. Wind speed, or air movement speed, or air mass flow around the leaves

The invention claimed is:

1. A greenhouse lighting control system for modulating growth or attributes of at least one plant comprising chlorophyll arranged in a greenhouse environment suitable for cultivating said at least one plant, said greenhouse environment being at least partly transmissive to ambient light, the system comprising:
   a plurality of light emitting devices arranged to emit light towards the at least one plant to thereby modulate plant growth by an alteration of photosynthesis, hormone regulation and/or secondary metabolites of the at least one plant, wherein a first of said plurality of light emitting devices is arranged to emit light of a first wavelength range and a second of said plurality of light emitting devices is arranged to emit light of a second wavelength range, wherein said first wavelength range is different from said second wavelength range,
   at least one light sensor arranged to detect light surrounding the at least one plant, said at least one light sensor being arranged to:
   measure light intensity in a wavelength range corresponding to chlorophyll fluorescence and/or to measure light intensity in a wavelength range corresponding to leaf light reflectance of said at least one plant, and
   based on said measured light intensity, determine data including a set of parameters including chlorophyll fluorescence and/or leaf light reflectance of said at least one plant,
   a processor, connected to said plurality of light emitting devices and to said at least one light sensor, and arranged to receive said data from the at least one light sensor and to control the plurality of light emitting devices,
   wherein the processor is configured to:
   generate a control signal based on the data and a reference, wherein said reference includes at least one of chlorophyll fluorescence and/or leaf light reflectance as an input, and
   apply the control signal to the plurality of light emitting devices to control the light emitted from the plurality of light emitting devices in order to modulate growth or attributes of said at least one plant.

2. The greenhouse lighting control system according to claim 1, wherein said at least one light sensor is arranged to detect light in wavelength ranges selected from 400-630 nm, 630-700 nm, 700-740 nm, 750-850 nm, 850-1400 nm, and 400-700 nm.

3. The greenhouse lighting control system according to claim 1, wherein said reference is a dynamic reference which may change over the course of plant growth.

4. The greenhouse lighting control system according to claim 1, wherein said first and said second wavelength ranges are selected from within the range of UV-B to IR.

5. The greenhouse lighting control system according to claim 1, wherein said at least one light sensor detects ambient light and light emitted from said plurality of light sources and reflected from the at least one or more plants.

6. The greenhouse lighting control system according to claim 1, wherein said at least one light sensor detects chlorophyll fluorescence emitted from the at least one plant.

7. The greenhouse lighting control system according to claim 1, wherein said at least one light sensor detects incident light.

8. The greenhouse lighting control system according to claim 1, further comprising a light sensor arranged to measure only ambient light.

9. The greenhouse lighting control system according to claim 1, wherein controlling the light emitted from the plurality of light emitting devices includes modifying at least one of an intensity, a frequency, and/or a duration of the light emitted by said light emitting devices.

10. The greenhouse lighting control system according to claim 1, further comprising at least one of a temperature sensor, a, humidity sensor, a $CO_2$ sensor, and/or an air flow sensor.

11. The greenhouse lighting control system according to claim 1, wherein said control signal additionally controls a desired level of carbon dioxide in said greenhouse.

12. The greenhouse lighting control system according to claim 11, wherein the processor is configured to generate a second control signal based on the reference and the data, and to apply said second control signal to a carbon dioxide control device in order to approach said desired level of carbon dioxide in said greenhouse.

13. A cabinet lighting control system for modulating growth or attributes of at least one plant comprising chlorophyll arranged in a closed environment in the absence of ambient light suitable for cultivating at least one plant comprising chlorophyll, the system comprising:
   a plurality of light emitting devices arranged to emit light towards the at least one plant to thereby modulate plant growth by an alteration of photosynthesis, hormone regulation and/or secondary metabolites of the at least one plant, wherein a first of said plurality of light emitting devices is arranged to emit light of a first wavelength range and a second of said plurality of light emitting devices is arranged to emit light of a second wavelength range, wherein said first wavelength range is different from said second wavelength range,
   at least one light sensor arranged to detect light surrounding the at least one plant, said at least one light sensor being arranged to:
   measure light intensity in a wavelength range corresponding to chlorophyll fluorescence and/or to measure light intensity in a wavelength range corresponding to leaf light reflectance of said at least one plant, and
   based on said measured light intensity, determine data including a set of parameters including chlorophyll fluorescence and/or leaf light reflectance of said at least one plant,
   a processor, connected to said plurality of fight emitting devices and to said at least one light sensor, and arranged to receive data from the at least one light sensor and to control the plurality of light emitting devices,
   wherein the processor is configured to:
   generate a control signal based on the data and a reference, wherein said reference includes at least one of chlorophyll fluorescence and/or leaf light reflectance as an input, and
   apply the control signal to the plurality of light emitting devices to control the light emitted from the plurality of light emitting devices in order to modulate growth or attributes of said at least one plant.

14. The cabinet lighting control system according to claim 13, wherein said at least one light sensor is arranged to detect light in wavelength ranges selected from 400-630 nm, 630-700 nm, 700-740 nm, 750-850 nm, 850-1400 nm, and 400-700 nm.

15. The cabinet lighting control system according to claim 13, wherein said reference is a dynamic reference which may change over the course of plant growth.

16. The cabinet lighting control system according to claim 13, wherein said first and said second wavelength ranges are selected from within the range of UV-B to IR.

17. The cabinet lighting control system according to claim 13, wherein said at least one light sensor detects chlorophyll fluorescence emitted from the at least one plant.

18. The cabinet lighting control system according to claim 13, wherein controlling the light emitted from the plurality of light emitting devices includes modifying at least one of an intensity, a frequency, and/or a duration of the light emitted by said light emitting devices.

19. The cabinet lighting control system according to claim 13, further comprising at least one of a temperature sensor, a humidity sensor, a CO2 sensor, and/or an air flow sensor.

20. The cabinet lighting control system according to claim 13, wherein said control signal additionally controls a desired level of carbon dioxide in said cabinet.

21. The cabinet lighting control system according to claim 20, wherein the processor is configured to generate a second control signal based on the reference and the data, and to apply said second control signal to a carbon dioxide control device in order to approach said desired level of carbon dioxide in said cabinet.

* * * * *